(12) United States Patent
Takahashi

(10) Patent No.: US 9,759,695 B2
(45) Date of Patent: Sep. 12, 2017

(54) COLUMN OVEN AND LIQUID CHROMATOGRAPH

(71) Applicant: SHIMADZU CORPORATION, Kyoto-shi, Kyoto (JP)

(72) Inventor: Kazuya Takahashi, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 526 days.

(21) Appl. No.: 14/455,388

(22) Filed: Aug. 8, 2014

(65) Prior Publication Data

US 2015/0059450 A1   Mar. 5, 2015

(30) Foreign Application Priority Data

Aug. 27, 2013   (JP) ................................. 2013-175917

(51) Int. Cl.
*G01N 30/30* (2006.01)
*F27B 17/02* (2006.01)
(Continued)

(52) U.S. Cl.
CPC ................ *G01N 30/30* (2013.01); *F27B 1/26* (2013.01); *F27B 5/18* (2013.01); *F27B 17/02* (2013.01);
(Continued)

(58) Field of Classification Search
None
See application file for complete search history.

(56) References Cited

U.S. PATENT DOCUMENTS

| 2006/0108350 A1* | 5/2006 | Yamauchi | .......... G05D 23/1931 |
| | | | 219/494 |
| 2010/0044288 A1* | 2/2010 | Kitagawa | ............... G01N 30/30 |
| | | | 210/149 |

(Continued)

FOREIGN PATENT DOCUMENTS

| CN | 101622535 A | 1/2010 |
| CN | 102262138 A | 11/2011 |
| JP | 3539093 B2 | 6/2004 |

OTHER PUBLICATIONS

Office Action dated Sep. 29, 2015, issued in counterpart Chinese Patent Application No. 201410409207.4, with English translation. (15 pages).

(Continued)

*Primary Examiner* — Joseph M Pelham
(74) *Attorney, Agent, or Firm* — Westerman, Hattori, Daniels & Adrian, LLP

(57) ABSTRACT

A column oven includes a main unit, an auxiliary unit, an outside sensor, an internal sensor, a temperature range holding section for holding a plurality of temperature ranges, a temperature range specifying portion for specifying the temperature range to which the outside temperature belongs, a temperature control program holding section for holding a temperature control program for a control method of the main unit and the auxiliary unit in each temperature range in such a way that outputs of the main unit and the auxiliary unit are continuous in the temperature ranges that are adjacent to each other, a control method setting portion for setting a control method of the main unit and the auxiliary unit based on the temperature range specified and the temperature control program, and a temperature control portion for controlling the main unit and the auxiliary unit.

14 Claims, 9 Drawing Sheets

(51) Int. Cl.
 *F27B 1/26* (2006.01)
 *F27B 5/18* (2006.01)
 *F27D 19/00* (2006.01)

(52) U.S. Cl.
 CPC ...... *F27D 19/00* (2013.01); *G01N 2030/3007* (2013.01); *G01N 2030/3053* (2013.01); *G01N 2030/3084* (2013.01)

(56) References Cited

U.S. PATENT DOCUMENTS

| | | | |
|---|---|---|---|
| 2010/0096380 A1* | 4/2010 | Satoh | G01N 30/30 219/400 |
| 2011/0290233 A1 | 12/2011 | Iso et al. | |
| 2013/0277350 A1* | 10/2013 | Arima | G01N 30/30 219/201 |
| 2014/0331744 A1* | 11/2014 | Van Egmond | G01N 30/12 73/23.41 |
| 2015/0233873 A1* | 8/2015 | Yanagisawa | G01N 30/88 702/24 |

OTHER PUBLICATIONS

Office Action dated Sep. 6, 2016, issued in counterpart Japanese Patent Application No. 2013-175917, with English translation. (5 pages).

* cited by examiner

COLUMN OVEN AND LIQUID CHROMATOGRAPH

BACKGROUND OF THE INVENTION

1. Field of the Invention

The present invention relates to a column oven for adjusting the temperature of an analytical column of a liquid chromatograph, and a liquid chromatograph using the column oven, and more particularly, to improvement of a temperature control method of the column oven.

2. Description of the Related Art

A liquid chromatograph includes an analytical column for separating a sample into components, and the separation performance of this analytical column greatly affects the analysis result. The separation performance of the analytical column is highly dependent on temperature, and there is a problem that if the temperature of the analytical column changes during an analysis, the reproducibility of the analysis result is impaired. Thus, the analytical column is placed inside a column oven, and the temperature inside the column oven is controlled to maintain a specific temperature (for example, see JP 3539093 B1).

A temperature sensor for detecting the inside temperature is provided to the column oven, and a heating device or a cooling device provided inside the column oven is controlled in such a way that the temperature detected by the temperature sensor is at a temperature set by an analyst. Controlling of the heating device and the cooling device is performed based on the inside temperature of the column oven, and, also, on the ambient temperature of the column oven (room temperature).

If the set temperature set by the analyst is much higher than the room temperature, the temperature inside the column oven is controlled by high output of the heating device, and if the set temperature is much lower than the room temperature, the temperature inside the column oven is controlled by high output of the cooling device. Moreover, if the set temperature is close to the room temperature, the temperature inside the column oven is controlled by turning on or off the heating device or the cooling device. In this manner, controlling of turning on or off, or controlling of the level of output is performed with respect to the heating device and the cooling device according to the relationship between the set temperature and the room temperature.

However, if the ambient temperature of the column oven changes during an analysis, the temperature inside the column oven may change and the stability may be impaired due to the relationship between the set temperature and the ambient temperature of the column oven being changed and the on/off of the heating device and the cooling device being suddenly switched or the output thereof being suddenly changed.

SUMMARY OF THE INVENTION

The present invention has its object to enable stable control of the temperature inside a column oven without being affected even if the temperature around the column oven changes during an analysis.

A column oven according to the present invention includes: a housing which includes a temperature adjusting space inside for accommodating an analytical column; a main unit for heating and cooling the analytical column in the temperature adjusting space; an auxiliary unit, provided separately from the main unit, for heating the analytical column in the temperature adjusting space; an outside sensor for detecting an outside temperature that is a temperature outside the housing; an internal sensor for detecting an inside temperature that is a temperature inside the temperature adjusting space; a set temperature holding section for holding a set temperature that is a target value of a temperature of the analytical column; a temperature range holding section for holding a plurality of continuous temperature ranges in a temperature scope in which the outside temperature possibly changes; a temperature range specifying portion for specifying, among the temperature ranges of the temperature range holding section, the temperature range to which the outside temperature detected by the outside sensor belongs; a temperature control program holding section for holding a temperature control program for a control method of the main unit and the auxiliary unit in each of the temperature ranges in such a way that outputs of the main unit and outputs of the auxiliary unit are continuous in the temperature ranges that are adjacent to each other; a control method setting portion for setting a control method of the main unit and the auxiliary unit based on the temperature range specified by the temperature range specifying portion and the temperature control program; and a temperature control portion for controlling the main unit and the auxiliary unit by using the control method set by the control method setting portion in such a way that the inside temperature is at the set temperature.

The "main unit for heating and cooling the analytical column in the temperature adjusting space" here includes, in addition to a unit that is in contact with the analytical column in the temperature adjusting space and that directly heats or cools the analytical column, a unit that heats or cools the analytical column by the main unit heating or cooling the air inside the temperature adjusting space.

In the same manner, the "auxiliary unit for heating the analytical column in the temperature adjusting space", includes, in addition to a unit that is in contact with the analytical column in the temperature adjusting space and that directly heats the analytical column, a unit that heats the analytical column by heating the air inside the temperature adjusting space.

According to the column oven of the present invention, the temperature control program is structured in such a way that the outputs of the main unit and the outputs of the auxiliary unit are continuous in the temperature ranges that are adjacent to each other, and the outputs of the main unit and the auxiliary unit are controlled based on the temperature control program, and thus, even if the temperature range to which the outside temperature belongs changes due to a change in the outside temperature, and the control method of the main unit and the auxiliary unit is changed accordingly, the outputs of the main unit and the auxiliary unit are not suddenly switched, and temperature inside the temperature adjusting space may be stably controlled.

A liquid chromatograph according to the present invention includes an analytical flow path, a liquid delivery section for delivering a mobile phase in the analytical flow path, a sample injection section for injecting a sample into the analytical flow path, an analytical column, provided on the analytical flow path, on a downstream side of the sample injection section, for separating the sample injected by the sample injection section into components, and a detector, provided on the analytical flow path, on a downstream side of the analytical column, for detecting a sample component separated by the analytical column, wherein the analytical column is accommodated inside a temperature adjusting space of a column oven of the present invention.

According to the liquid chromatograph of the present invention, since the analytical column is accommodated inside the column oven of the present invention, the temperature of the analytical column may be stably controlled even if the temperature around the device is changed, and the reproducibility of an analysis result may be improved.

DETAILED DESCRIPTION OF THE PREFERRED EMBODIMENTS

Figure 1:
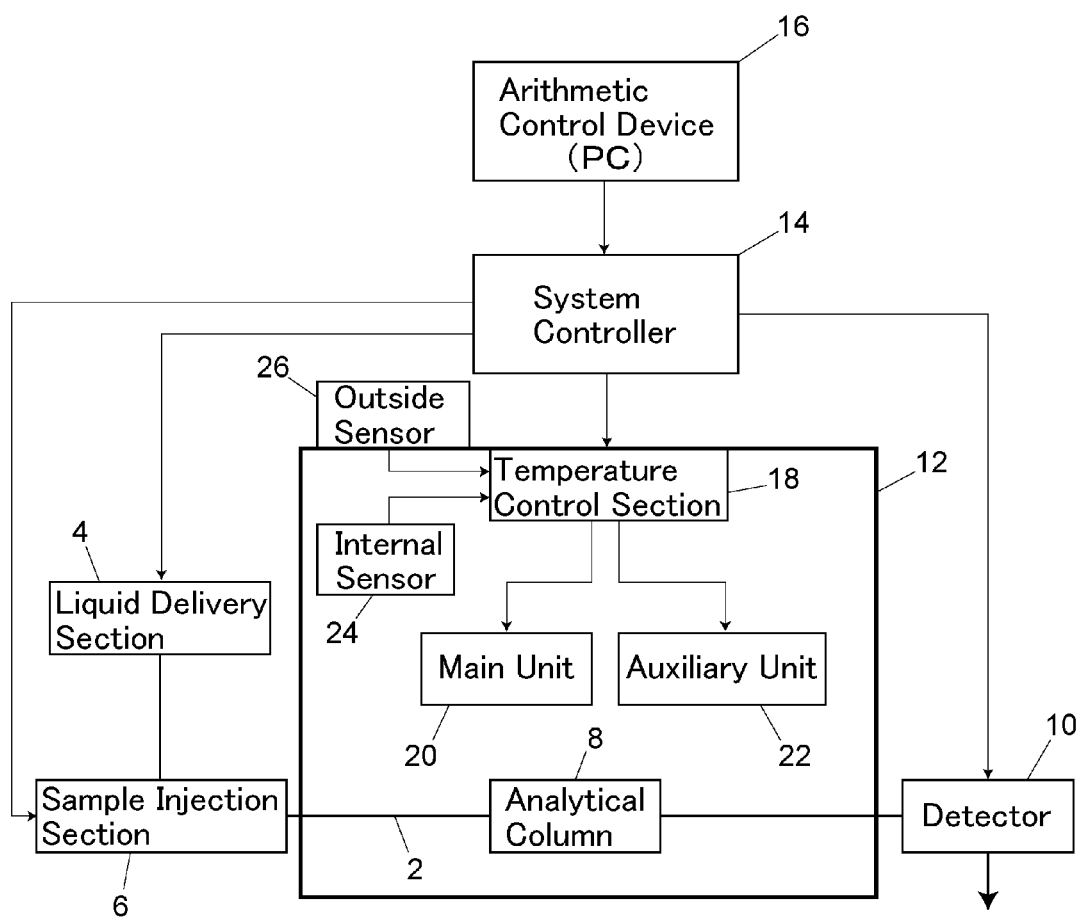
FIG. 1 is a block diagram schematically showing an example of a liquid chromatograph.

According to a preferred embodiment of a column oven of the present invention, a temperature range holding section includes, as temperature ranges, a set temperature-neighborhood range that is a temperature range having a specific temperature difference to a set temperature, a first heating range that is a temperature range that is continuous to the set temperature-neighborhood range and that is lower than the set temperature, a second heating range that is a temperature range that is continuous to the first heating range and that is lower than the first heating range, and a cooling range that is a temperature range that is continuous to the set temperature-neighborhood range and that is higher than the set temperature, and a temperature control program is structured to set, as a control method of a main unit and an auxiliary unit, a fine control method of heating by the auxiliary unit while cooling by the main unit when the temperature range to which the outside temperature belongs is the set temperature-neighborhood range, a first heating control method of stopping outputs of heating and cooling of the main unit and adjusting only a heating output of the auxiliary unit when the temperature range to which the outside temperature belongs is the first heating range, a second heating control method of simultaneously adjusting a heating output of the main unit and the heating output of the auxiliary unit when the temperature range to which the outside temperature belongs is the second heating range, and a cooling control method of stopping the heating output of the auxiliary unit and adjusting only a cooling output of the main unit when the temperature range to which the outside temperature belongs is the cooling range.

According to the embodiment described above, the main unit is configured to stop in the first heating range, and even if the outside temperature changes and the control method of the main unit and the auxiliary unit is changed between the fine control method and the second heating control method, the main unit is not suddenly switched from a heating output state to a cooling output state or from the cooling output state to the heating output state, and the temperature of the temperature adjusting space may be prevented from becoming unstable due to switching of heating and cooling of the main unit. Also, since the main unit is left without being used when the outside temperature is in the first heating range, the life of the main unit may be increased. The fine control method is for heating by the auxiliary unit while cooling by the main unit, and thus, the on/off of the main unit and the auxiliary unit is not switched when the outside temperature is in the set temperature-neighborhood range, and the temperature of the temperature adjusting space may be stably controlled.

Furthermore, in the embodiment described above, the second heating control method preferably reduces the heating output of the main unit and increases the heating output of the auxiliary unit as the outside temperature rises in the second heating range, in such a way that the heating output of the main unit is zero when the outside temperature is at a boundary temperature between the second heating range and the first heating range. Then, even if the outside temperature changes during an analysis, and the control method is switched between the first heating control method and the second heating control method, the main unit and the auxiliary unit are not suddenly switched off from a high output state or suddenly switched from an off state to a high output state, and the temperature inside the housing may be prevented from changing due to the sudden switching of the main unit and the auxiliary unit. Accordingly, the temperature of the temperature adjusting space may be stably controlled even when the outside temperature changes.

Also, the fine control method preferably controls the main unit and the auxiliary unit to increase the cooling output of the main unit and reduce the heating output of the auxiliary unit as the outside temperature rises in the set temperature-neighborhood range, in such a way that the heating output of the auxiliary unit is zero when the outside temperature is at a boundary temperature between the set temperature-neighborhood range and the cooling range. Then, even if the outside temperature changes from the set temperature-neighborhood range to the cooling range, and the control method is switched from the fine control method to the cooling control method, the auxiliary unit is not suddenly switched off, and the temperature of the temperature adjusting space may be stably controlled.

The temperature range holding section may include, as the temperature range, a third heating range that is a temperature range that is continuous to the second heating range and that is lower than the second heating range, and when the temperature range to which the outside temperature belongs is the third heating range, the temperature control program may set, as the control method of the main unit and the auxiliary unit, a third heating control method of adjusting only the heating output of the main unit while stopping the heating output of the auxiliary unit. Then, since only the main unit is used in the third heating range where a high heating output is required, the auxiliary unit may be left unused, and the life of the auxiliary unit may be increased.

The temperature range holding section may divide and hold the set temperature-neighborhood range as a first set temperature-neighborhood range that is lower than the set temperature and a second set temperature-neighborhood range that is higher than the set temperature. The temperature control program may set, as the control method of the main unit and the auxiliary unit, a first fine control method of adjusting the cooling output of the main unit while maintaining a steady heating output of the auxiliary unit when the temperature range to which the outside temperature belongs is the first set temperature-neighborhood range, and a second fine control method of adjusting the heating output of the auxiliary unit while maintaining a steady cooling output of the main unit when the temperature range to which the outside temperature belongs is the second set temperature-neighborhood range. Since the temperature of the temperature adjusting space is controlled by adjusting the output of only one of the main unit and the auxiliary unit, controlling the main unit and the auxiliary unit when the outside temperature is in the first set temperature-neighborhood range or in the second set temperature-neighborhood range is facilitated.

In the following, examples of the liquid chromatograph and the column oven will be described with reference to the drawings.

The liquid chromatograph includes a liquid delivery section 4 for delivering a mobile phase in an analytical flow path 2, a sample injection section 6 configured from an autosampler for injecting a sample into the analytical flow path 2, an analytical column 8 for separating a sample injected into the analytical flow path 2 by the sample injection section 6 into components, and a detector 10 for detecting a sample component separated by the analytical column 8. The analytical column 8 is accommodated inside a column oven 12 (the temperature adjusting space).

The liquid delivery section 4, the sample injection section 6, the detector 10, and the column oven 12 are controlled by a system controller 14. An arithmetic control device 16 that is realized by, for example, a personal computer (PC), is connected to the system controller 14. When an analyst inputs, to the arithmetic control device 16, information about the flow rate of the mobile phase or a sample, or an analysis condition such as the set temperature of the column oven 12, such information is given to the system controller 14, and the system controller 14 controls the operations of the liquid delivery section 4, the sample injection section 6, the detector 10, and the column oven 12 based on the information.

The temperature of the analytical column 8 set by an analyst (the set temperature) is given to a temperature control section 18 of the column oven 12 by the system controller 14. Inside the column oven 12, a main unit 20 and an auxiliary unit 22 are provided as temperature adjusting devices for heating or cooling the analytical column 8, and also, an internal sensor 24 for detecting the temperature (the inside temperature) of the temperature adjusting space inside the column oven 12 is provided. The main unit 20 is a device capable of both heating and cooling, such as a Peltier device. The auxiliary unit 22 is a heat generating device for heating.

The temperature control section 18 controls the outputs of the main unit 20 and the auxiliary unit 22 based on a signal of the internal sensor 24 and a signal of an outside sensor 26 for detecting the temperature outside the column oven 12 (for example, an air temperature outside the column oven 12). In FIG. 1, the outside sensor 26 is shown being attached to outside the housing of the column oven 12, but the outside sensor 26 may be provided to a device different from the column oven 12, such as the liquid delivery section 4, the sample injection section 6, or the detector 10. In this case, the detection signal of the outside sensor 26 is fed to the temperature control section 18 via the system controller 14.

A detection signal obtained by the detector 10 is fed to the arithmetic control device 16 via the system controller 14. The arithmetic control device 16 performs arithmetic computation for performing identification or quantitative determination of sample components based on the detection signal which has been fed.

Now, the column oven 12 will be described with reference to FIGS. 3 and 4.

Figure 3:
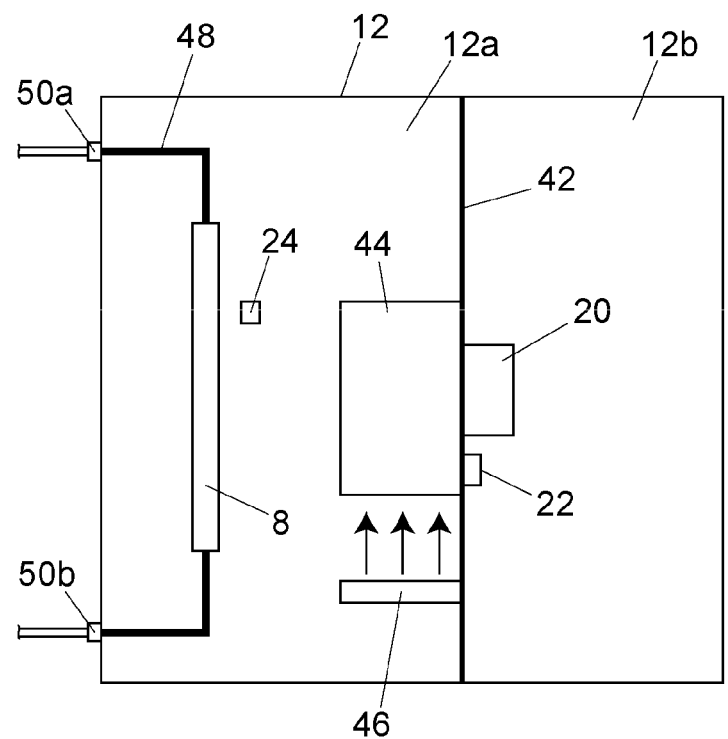
FIG. 3 is a schematic configuration diagram showing an example of a column oven.
Figure 4:
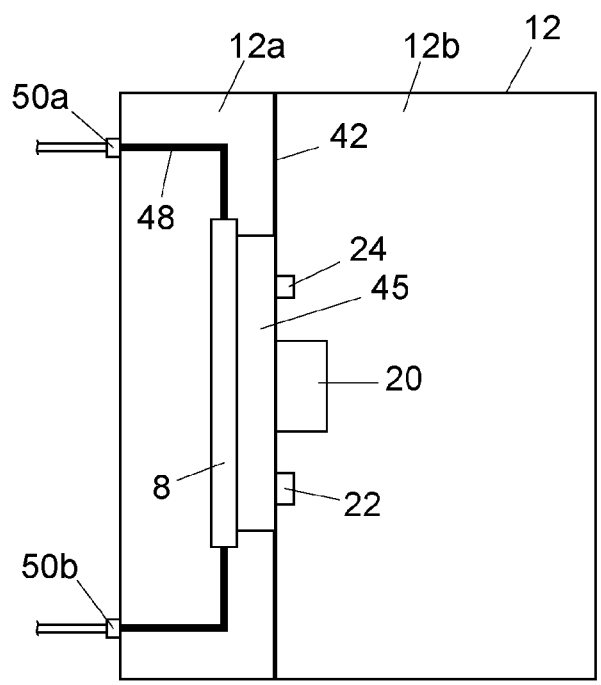
FIG. 4 is a schematic configuration diagram showing another example of the column oven.

FIG. 3 shows an example of a column oven of an air temperature adjustment method, and FIG. 4 shows an example of a column oven of a block heating method. The present invention may be applied to the column oven of either method.

A column oven 12 of an air temperature adjustment method shown in FIG. 3 includes an analytical column 8 arranged inside a temperature adjusting space 12*a* provided inside the housing, and an internal sensor 24, a heat sink fin 44, and a fan 46 arranged inside the same temperature adjusting space 12*a*. The analytical column 8 is connected to an inlet port 50*a* and an outlet port 50*b* provided on an outer panel of the housing by a pipe 48. A pipe from the sample injection section 6 is connected to the inlet port 50*a*, and a pipe that leads to the detector 10 is connected to the outlet port 50*b*. The internal sensor 24 is arranged near the analytical column 8.

A main unit 20 configured from a Peltier device and an auxiliary unit 22 configured from a heat generating device are arranged in a space 12*b* different from the temperature adjusting space 12*a* inside the housing of the column oven 12. The temperature adjusting space 12*a* and the space 12*b* are thermally separated by a heat insulating partition 42, and the heat sink fin 44 is attached to the partition 42 on the side of the temperature adjusting space 12*a*, and the main unit 20 and the auxiliary unit 22 are attached to the partition 42 on the side of the space 12*b*.

The main unit 20 and the auxiliary unit 22 are adhered to the heat sink fin 44, and the main unit 20 is capable of directly heating or cooling the heat sink fin 44, and the auxiliary unit 22 is capable of directly heating the heat sink fin 44. The heat sink fin 44 is formed from a plurality of metal plates arranged with gaps therebetween. The fan 46 blows air to the heat sink fin 44, and causes air heated or cooled by passing through the gaps of the metal plates of the heat sink fin 44 to circulate inside the temperature adjusting space 12*a*. That is, this column oven 12 of the air temperature adjustment method controls the temperature of the analytical column 8 to the set temperature by heating or cooling the whole air inside the temperature adjusting space 12*a*.

The main unit 20 is configured to have the temperature on the surface opposite the surface that is in contact with the heat sink fin 44 lowered at the time of heating the heat sink fin 44, and to discharge heat conducted away from the heat sink fin 44 from the surface opposite the surface that is in contact with the heat sink fin 44 at the time of cooling the heat sink fin 44, but since the space 12*b* where the main unit 20 is arranged is thermally separated from the temperature adjusting space 12*a*, the temperature inside the temperature adjusting space 12*a* is not affected.

A column oven 12 of a block heating method shown in FIG. 4 is configured to heat or cool a thermally conductive column holder 45 attached to a partition 42 on the side of a temperature adjusting space 12*a* by a main unit 20 and an auxiliary unit 22 attached to the partition 42 on the side of a space 12*b*. The column holder 45 is adhered to an analytical column 8 and holds the analytical column 8. An internal sensor 24 detects the temperature of the column holder 45. That is, this column oven 12 of the block heating method controls the temperature of the analytical column 8 to the set temperature by heating or cooling the thermally conductive column holder 45 holding the analytical column 8.

Figure 2:
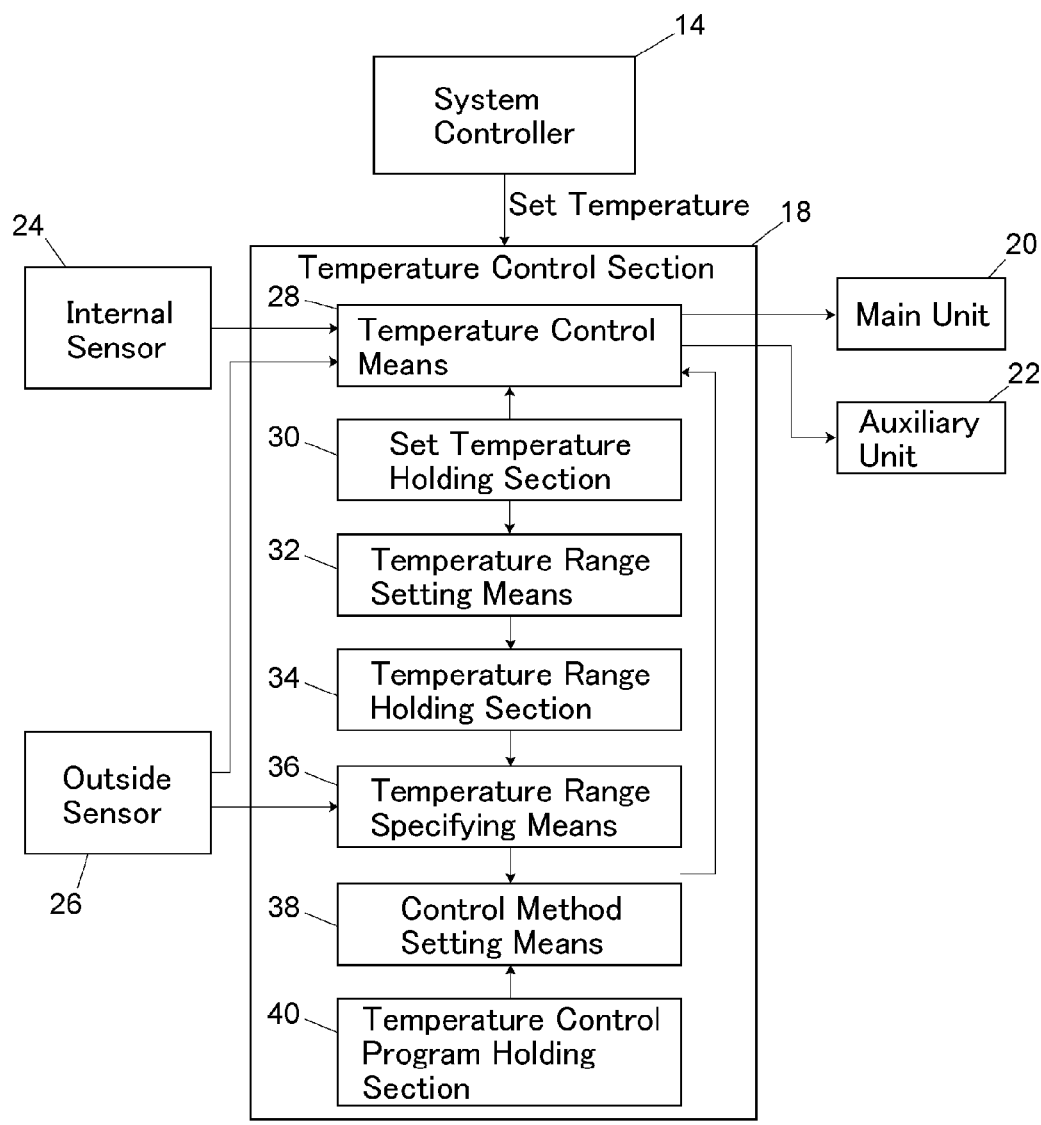
FIG. 2 is a block diagram showing a control system of the present example.

Controlling of the main unit 20 and the auxiliary unit 22 by the temperature control section 18 of the column oven 12 will be described with reference to FIG. 2.

The temperature control section 18 is realized by a computer, and includes a temperature control portion 28, a set temperature holding section 30, a temperature range setting portion 32, a temperature range holding section 34, a temperature range specifying portion 36, a control method setting portion 38, and a temperature control program holding section 40.

A set temperature set by an analyst is provided to the temperature control section 18 via the system controller 14, and is stored in the set temperature holding section 30. The temperature control portion 28 controls the outputs of the main unit 20 and the auxiliary unit 22 in such a way that the inside temperature is at the set temperature, based on the set temperature stored in the set temperature holding section 30, the inside temperature obtained by the internal sensor 24, the outside temperature obtained by the outside sensor 26, and a control method set by the control method setting portion 38 described later.

The temperature range setting portion 32 is for setting a "temperature range", to be used as a reference in the control method of the main unit 20 and the auxiliary unit 22 based on the set temperature.

Here, the "temperature range" will be described with reference to FIG. 6.

The "temperature range" indicates the relation of the outside temperature to the set temperature. In the example of FIG. 6, temperature ranges (1) to (6) are set with reference to the set temperature.

Ranges (1) and (2) are set temperature-neighborhood ranges that are temperature ranges near the set temperature. The range (1) is a first set temperature-neighborhood range, and is a temperature range lower than the set temperature, of the set temperature-neighborhood ranges. The range (2) is a second set temperature-neighborhood range, and is a temperature range higher than the set temperature, of the set temperature-neighborhood ranges.

The range (3) is a first heating range, and is a temperature range that is continuous to the first set temperature-neighborhood range (1) and that is lower than the first set temperature-neighborhood range (1).

The range (4) is a second heating range, and is a temperature range that is continuous to the first heating range (3) and that is even lower than the first heating range (3).

The range (5) is a third heating range, and is a temperature range that is continuous to the second heating range (4) and that is even lower than the second heating range (4).

The range (6) is a cooling range, and is a temperature range that is continuous to the second set temperature-neighborhood range (2) and that is higher than the second set temperature-neighborhood range (2).

Referring back to FIG. 2, the temperature range setting portion 32 is configured to set the temperature ranges (1) to (6) with reference to a set temperature which has been acquired. For example, a temperature range of the set temperature to minus 5° C. of the set temperature is set as the first set temperature-neighborhood range (1), a temperature range of the set temperature to plus 5° C. of the set temperature is set as the second set temperature-neighborhood range (2), a temperature range of minus 5° C. to minus 10° C. of the set temperature is set as the first heating range (3), a temperature range of minus 10° C. to minus 16° C. of the set temperature is set as the second heating range (4), a temperature range lower than minus 16° C. of the set temperature is set as the third heating range (5), and a temperature range higher than plus 5° C. of the set temperature is set as the cooling range (6). The temperature ranges set by the temperature range setting portion 32 are stored in the temperature range holding section 34.

The temperature range specifying portion 36 is for acquiring the outside temperature from the outside sensor 26, and for specifying the temperature range to which the outside temperature belongs.

The control method setting portion 38 is for setting a control method according to the temperature range specified by the temperature range specifying portion 36. A control method to be used in the temperature range to which the outside temperature belongs is stored in the temperature control program holding section 40 as a temperature control program. The control method setting portion 38 sets a control method of the main unit 20 and the auxiliary unit 22 according to the temperature range to which the outside temperature belongs based on the temperature control program. The temperature control portion 28 is configured to control the main unit 20 and the auxiliary unit 22 according to the control method set by the control method setting portion 38.

Figure 5:
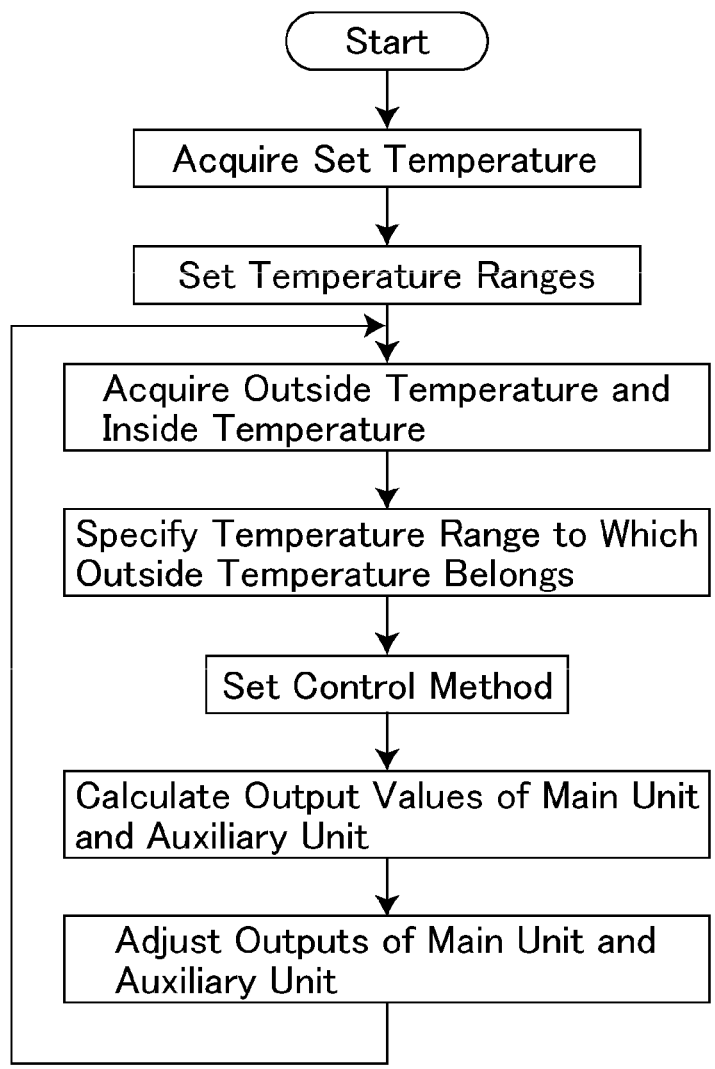
FIG. 5 is a flow chart for describing an example of temperature control of the column oven.

The flow of controlling the temperature of the analytical column 8 by the temperature control section 18 will be described with reference to FIG. 5.

First, the temperature control section 18 acquires the set temperature of the column oven 12 set by an analyst via the system controller 14. When the set temperature is acquired, the temperature range setting portion 32 sets the temperature ranges based on the set temperature, and the temperature range holding section 34 stores the temperature ranges.

Next, the inside temperature is acquired from the internal sensor 24, and the outside temperature is acquired from the outside sensor 26. The temperature range specifying portion 36 specifies the temperature range to which the outside temperature which has been acquired belongs based on the difference between the outside temperature and the set temperature, for example. The control method setting portion 38 acquires a control method according to the temperature range to which the outside temperature belongs by using the temperature control program held in the temperature control program holding section 40, and sets the same as the control method of the main unit 20 and the auxiliary unit 22.

The temperature control portion 28 calculates output values of the main unit 20 and the auxiliary unit 22 according to the control method which has been set, in such a way that the internal temperature will be at the set temperature, and adjusts the outputs of the main unit 20 and the auxiliary unit 22 to the calculated output values.

Thereafter, the inside temperature and the outside temperature are acquired at regular intervals from the internal sensor 24 and the outside sensor 26, and specification of the temperature range, setting of the control method, and adjustment of the outputs of the main unit 20 and the auxiliary unit 22 are performed each time.

A preferred example of the temperature control program will be described with reference to FIG. 6.

This temperature control program is configured to cause the outputs of the main unit 20 and the outputs of the auxiliary unit 22 to be continuous in the temperature ranges that are adjacent to each other. That is, even if the outside temperature changes, and the temperature range to which the outside temperature belongs changes, the main unit 20 and the auxiliary unit 22 are not suddenly switched from a high output state to an off state or from an off state to a high output state, and the output of the main unit 20 is not suddenly switched from heating to cooling or from cooling to heating. In the following, the control method to be used in each temperature range will be concretely described.

In the first set temperature-neighborhood range (1), the first fine control method of performing feedback control on the cooling output of the main unit 20 based on the inside temperature detected by the internal sensor 24 while maintaining the output of the auxiliary unit 22 at a constant value obtained by an experiment or the like is used. According to this first fine control method, the cooling output of the main unit 20 is increased as the outside temperature rises.

In the second set temperature-neighborhood range (2), the second fine control method of performing feedback control on the output of the auxiliary unit 22 based on the inside temperature detected by the internal sensor 24 while maintaining the cooling output of the main unit 20 at a constant value obtained by an experiment of the like is used. According to this second fine control method, the output of the auxiliary unit 22 is reduced as the outside temperature rises. The cooling output of the main unit 20 is in such a way that, when the outside temperature is at the temperature of the boundary to the cooling range (6), the output of the auxiliary unit 22 is zero.

In the first heating range (3), the first heating control method of stopping the main unit 20, and performing feedback control on the output of the auxiliary unit 22 based on the inside temperature detected by the internal sensor 24 is used. According to this first heating control method, the output of the auxiliary unit 22 is reduced as the outside temperature rises.

In the second heating range (4), the second heating control method of performing feedback control on the heating output of the main unit 20 based on the inside temperature detected by the internal sensor 24, and controlling the output of the auxiliary unit 22 to a predetermined value according to the outside temperature is used. The output of the auxiliary unit 22 is set in advance to be linearly increased as the outside temperature rises in such a way that, when the outside temperature is at the temperature of the boundary to the third heating range (5), the output is zero, and when the outside temperature is at the temperature of the boundary to the first heating range (3), the output is of a value by which the inside temperature may be controlled solely by the output (with the main unit 20 in the off state) (for example, 50% of the maximum output of the auxiliary unit 22). That is, the output of the auxiliary unit 22 may be obtained by linear calculation based on the outside temperature regardless of the inside temperature. The heating output of the main unit 20 is reduced as the outside temperature rises, and is zero when the outside temperature is at the temperature of the boundary to the first heating range.

In the third heating range (5), the third heating control method of stopping the auxiliary unit 22, and performing feedback control on the heating output of the main unit 20 based on the inside temperature detected by the internal sensor 24 is used. According to this third heating control method, the heating output of the main unit 20 is reduced as the outside temperature rises.

In the cooling range (6), the cooling control method of stopping the auxiliary unit 22, and performing feedback control on the cooling output of the main unit 20 based on the inside temperature detected by the internal sensor 24 is used. According to this cooling control method, the cooling output of the main unit 20 is increased as the outside temperature rises.

Figure 7:
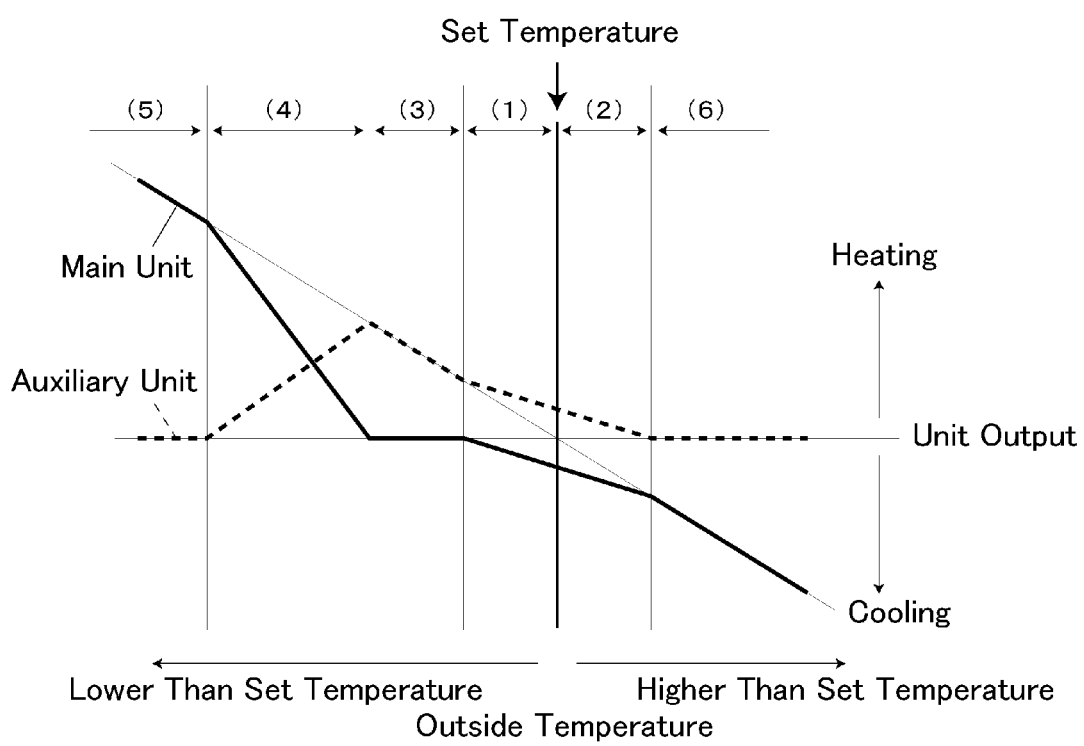
FIG. 7 is a graph showing another example of the temperature control program.

Additionally, as shown in FIG. 7, feedback control may be performed, in the set temperature-neighborhood ranges (1) and (2), on both the cooling output of the main unit 20 and the output of the auxiliary unit 22 based on the inside temperature detected by the internal sensor 24. In this case, the cooling output of the main unit 20 is increased and the output of the auxiliary unit 22 is reduced as the outside temperature rises. Also according to this configuration, the outputs of the main unit 20 and the auxiliary unit 22 will be continuous in the temperature ranges that are adjacent to each other.

Figure 8:
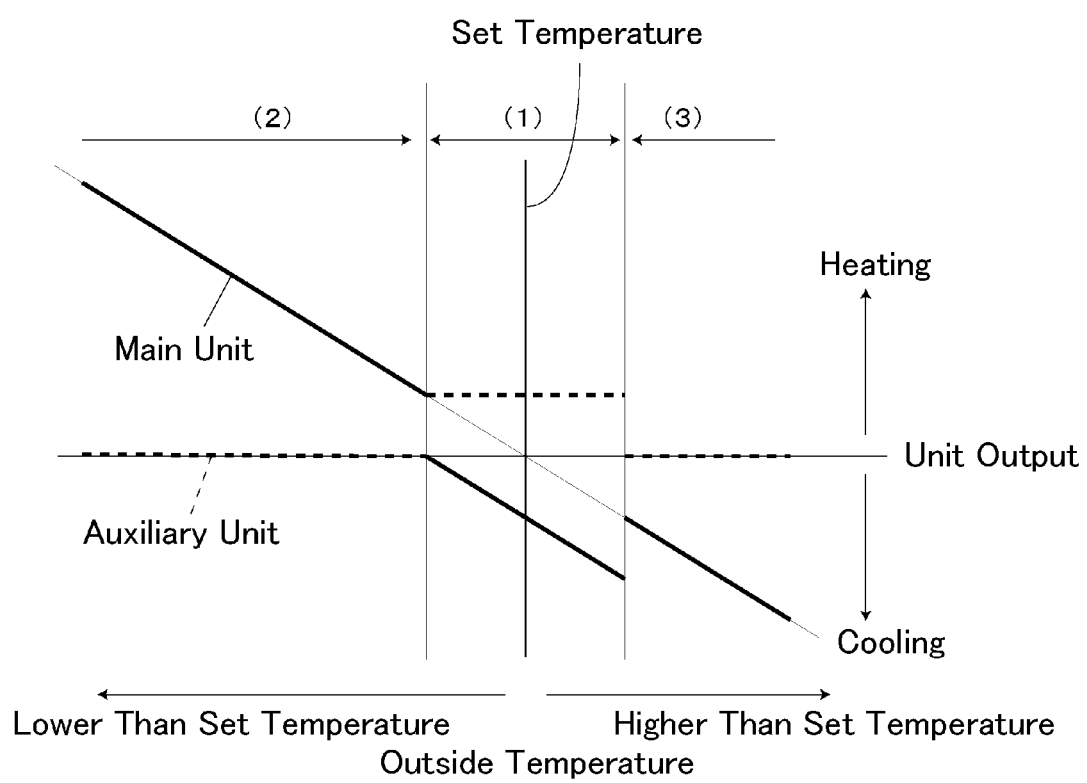
FIG. 8 is a graph showing a comparative example of the temperature control program.

FIG. 8 shows a comparative example of the temperature control program.

According to this temperature control program, three temperature ranges (1) to (3) are set. In a set temperature-neighborhood range (1), which is a temperature range around the set temperature, a control method of keeping the output of the auxiliary unit 22 constant, and performing feedback control on the cooling output of the main unit 20 based on the inside temperature detected by the internal sensor 24 is used. In a heating range (2) lower than the set temperature-neighborhood range (1), a control method of stopping the auxiliary unit 22, and performing feedback control on the heating output of the main unit 20 based on the inside temperature detected by the internal sensor 24 is used. In a cooling range (3) higher than the set temperature-neighborhood range (1), a control method of stopping the auxiliary unit, and performing feedback control on the cooling output of the main unit 20 based on the inside temperature detected by the internal sensor 24 is used.

According to the temperature control program of FIG. 8, if, for example, the outside temperature belonging to the heating range (2) changes to belong to the set temperature-neighborhood range (1), the main unit 20 performing heating output is switched to perform cooling output, and the auxiliary unit 22 which is stopped is caused to be in a state of output of a specific level, and thus, controlling of the temperature inside the column oven 12 becomes unstable at the timing of switching. The same can be said for a case where the temperature range to which the outside temperature belongs changes between the set temperature-neighborhood range (1) and the cooling range (3). In this manner, if the outputs of the main unit 20 and the auxiliary unit 22 are not continuous in the temperature ranges that are adjacent to each other, controlling of the temperature inside the column oven 12 becomes unstable when the outside temperature changes across the boundary temperature of the temperature ranges, thereby affecting the analysis.

Figure 9:
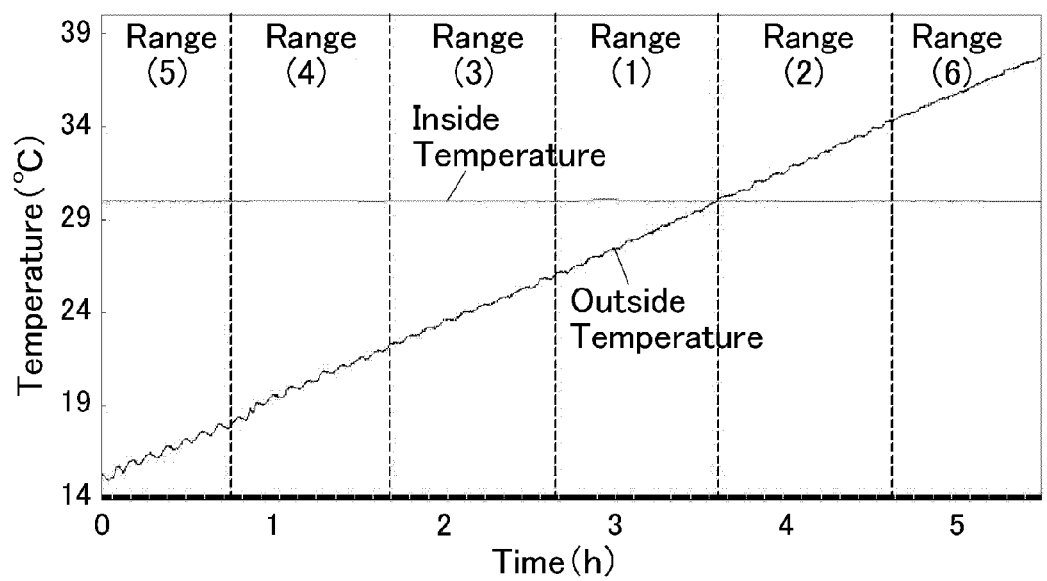
FIG. 9 is a graph showing a relationship between the outside temperature and the temperature inside the column oven in the case of using a temperature control program of an example.
Figure 10:
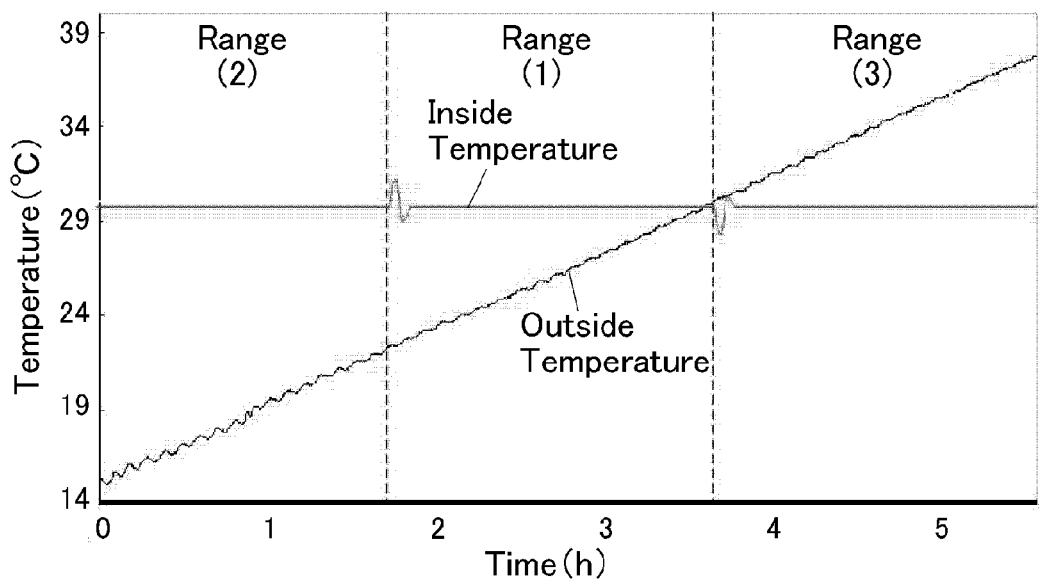
FIG. 10 is a graph showing a relationship between the room temperature and the temperature inside the column oven in the case of using a temperature control program of a comparative example.

FIGS. 9 and 10 are data showing the results of experiments for comparing the stability of controlling of the temperature inside the column oven 12 by the temperature control programs. FIG. 9 is data of the result of an experiment conducted using the temperature control program of FIG. 6, and FIG. 10 is data of the result of an experiment conducted using the temperature control program of FIG. 8. These experiments were conducted by setting the set temperature of the column oven 12 to 30° C. and the outside temperature (the room temperature) at the start of the experiments to 15° C., and measuring the temperature inside the column oven 12 (the inside temperature) while raising the outside temperature to 39° C.

Figure 6:
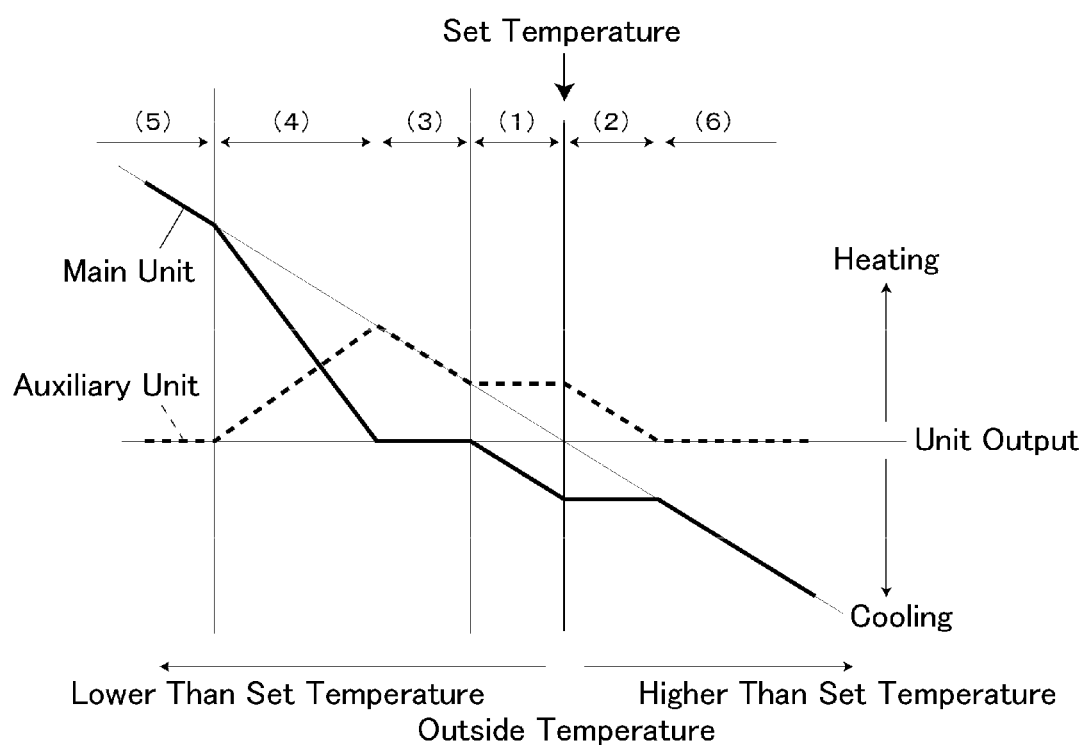
FIG. 6 is a graph showing an example of a temperature control program.

In the case where the temperature control program of FIG. 6 is used, when the outside temperature is gradually raised from 15° C., the temperature range to which the outside temperature belongs changes from the third heating range (5) to the second heating range (4), the first heating range (3), the first set temperature-neighborhood range (1), the second set temperature-neighborhood range (2), and the cooling range (6) in this order, and the control method of the main unit 20 and the auxiliary unit 22 is changed accordingly. However, as shown in FIG. 9, the temperature inside the column oven 12 is maintained substantially constant at 30° C., which is the set temperature, and is not affected by the change of the control method.

On the other hand, in the case where the temperature control program of FIG. 8 is used, the temperature inside the column oven 12 changes at the time of the temperature range to which the outside temperature belongs changing from the heating range (2) to the set temperature-neighborhood range (1) and from the set temperature-neighborhood range (1) to the cooling range (3), and it can be seen that control of the temperature inside the column oven 12 becomes unstable due to the change of the control method of the main unit 20 and the auxiliary unit 22.

What is claimed is:

1. A column oven comprising:
   a housing including inside a temperature adjusting space for accommodating an analytical column;
   a main unit for heating and cooling the analytical column in the temperature adjusting space;
   an auxiliary unit, provided separately from the main unit, for heating the analytical column in the temperature adjusting space;
   an outside sensor for detecting an outside temperature that is a temperature outside the housing;
   an internal sensor for detecting an inside temperature that is a temperature inside the temperature adjusting space;
   a set temperature holding section for holding a set temperature that is a target value of a temperature of the analytical column;
   a temperature range holding section for holding a plurality of continuous temperature ranges in a temperature scope in which the outside temperature possibly changes;
   a temperature range specifying portion for specifying, among the temperature ranges of the temperature range holding section, the temperature range to which the outside temperature detected by the outside sensor belongs;
   a temperature control program holding section for holding a temperature control program for a control method of the main unit and the auxiliary unit in each of the temperature ranges in such a way that outputs of the main unit and outputs of the auxiliary unit are continuous as a temperature passes from one of the temperature ranges to an adjacent temperature range;
   a control method setting portion for setting a control method of the main unit and the auxiliary unit based on the temperature range specified by the temperature range specifying portion and the temperature control program; and
   a temperature control portion for controlling the main unit and the auxiliary unit by using the control method set by the control method setting portion in such a way that the inside temperature is at the set temperature.

2. The column oven according to claim 1,
   wherein the temperature range holding section includes, as the temperature ranges, a set temperature-neighborhood range that is a temperature range having a specific temperature difference to the set temperature, a first heating range that is a temperature range that is continuous to the set temperature-neighborhood range and that is lower than the set temperature, a second heating range that is a temperature range that is continuous to the first heating range and that is lower than the first heating range, and a cooling range that is a temperature range that is continuous to the set temperature-neighborhood range and that is higher than the set temperature, and
   wherein the temperature control program is structured to set, as the control method of the main unit and the auxiliary unit, a fine control method of heating by the auxiliary unit while cooling by the main unit when the temperature range to which the outside temperature belongs is the set temperature-neighborhood range, a first heating control method of stopping outputs of heating and cooling of the main unit and adjusting only a heating output of the auxiliary unit when the temperature range to which the outside temperature belongs is the first heating range, a second heating control method of simultaneously adjusting a heating output of the main unit and the heating output of the auxiliary unit when the temperature range to which the outside temperature belongs is the second heating range, and a cooling control method of stopping the heating output of the auxiliary unit and adjusting only a cooling output of the main unit when the temperature range to which the outside temperature belongs is the cooling range.

3. The column oven according to claim 2,
   wherein the second heating control method reduces the heating output of the main unit and increases the heating output of the auxiliary unit as the outside temperature rises in the second heating range, in such a way that the heating output of the main unit is zero when the outside temperature is at a boundary temperature between the second heating range and the first heating range.

4. The column oven according to claim 2,
   wherein the fine control method increases the cooling output of the main unit and reduces the heating output of the auxiliary unit as the outside temperature rises in the set temperature-neighborhood range, in such a way that the heating output of the auxiliary unit is zero when the outside temperature is at a boundary temperature between the set temperature-neighborhood range and the cooling range.

5. The column oven according to claim 2,
   wherein the temperature range holding section includes, as the temperature range, a third heating range that is a temperature range that is continuous to the second heating range and that is lower than the second heating range, and
   wherein, when the temperature range to which the outside temperature belongs is the third heating range, the temperature control program sets, as the control method of the main unit and the auxiliary unit, a third heating control method of adjusting only the heating output of the main unit while stopping the heating output of the auxiliary unit.

6. The column oven according to claim 2,
   wherein temperature range holding section divides and holds the set temperature-neighborhood range as a first set temperature-neighborhood range that is a temperature range that is lower than the set temperature and a second set temperature-neighborhood range that is a temperature range that is higher than the set temperature, and wherein the temperature control program sets, as the control method of the main unit and the auxiliary unit, a first fine control method of adjusting the cooling output of the main unit while maintaining constant the heating output of the auxiliary unit when the temperature range to which the outside temperature belongs is the first set temperature-neighborhood range, and a second fine control method of adjusting the heating output of the auxiliary unit while maintaining constant the cooling output of the main unit when the temperature range to which the outside temperature belongs is the second set temperature-neighborhood range.

7. The column oven according to claim 1, further comprising:

a temperature range setting portion for setting the temperature ranges based on the set temperature, and causing the temperature range holding section to hold the temperature ranges.

8. A liquid chromatograph comprising:

an analytical flow path;

a liquid delivery section for delivering a mobile phase in the analytical flow path;

a sample injection section for injecting a sample into the analytical flow path;

an analytical column, provided on the analytical flow path, on a downstream side of the sample injection section, for separating the sample injected by the sample injection section into components; and a detector, provided on the analytical flow path, on a downstream side of the analytical column, for detecting a sample component separated by the analytical column, wherein the analytical column is accommodated inside a temperature adjusting space of a column oven according to claim 1.

9. The liquid chromatograph according to claim 8, wherein the temperature range holding section includes, as the temperature ranges, a set temperature-neighborhood range that is a temperature range having a specific temperature difference to the set temperature, a first heating range that is a temperature range that is continuous to the set temperature-neighborhood range and that is lower than the set temperature, a second heating range that is a temperature range that is continuous to the first heating range and that is lower than the first heating range, and a cooling range that is a temperature range that is continuous to the set temperature-neighborhood range and that is higher than the set temperature, and wherein the temperature control program is structured to set, as the control method of the main unit and the auxiliary unit, a fine control method of heating by the auxiliary unit while cooling by the main unit when the temperature range to which the outside temperature belongs is the set temperature-neighborhood range, a first heating control method of stopping outputs of heating and cooling of the main unit and adjusting only a heating output of the auxiliary unit when the temperature range to which the outside temperature belongs is the first heating range, a second heating control method of simultaneously adjusting a heating output of the main unit and the heating output of the auxiliary unit when the temperature range to which the outside temperature belongs is the second heating range, and a cooling control method of stopping the heating output of the auxiliary unit and adjusting only a cooling output of the main unit when the temperature range to which the outside temperature belongs is the cooling range.

10. The liquid chromatograph according to claim 9, wherein the second heating control method reduces the heating output of the main unit and increases the heating output of the auxiliary unit as the outside temperature rises in the second heating range, in such a way that the heating output of the main unit is zero when the outside temperature is at a boundary temperature between the second heating range and the first heating range.

11. The liquid chromatograph according to claim 9, wherein the fine control method increases the cooling output of the main unit and reduces the heating output of the auxiliary unit as the outside temperature rises in the set temperature-neighborhood range, in such a way that the heating output of the auxiliary unit is zero when the outside temperature is at a boundary temperature between the set temperature-neighborhood range and the cooling range.

12. The liquid chromatograph according to claim 9, wherein the temperature range holding section includes, as the temperature range, a third heating range that is a temperature range that is continuous to the second heating range and that is lower than the second heating range, and wherein, when the temperature range to which the outside temperature belongs is the third heating range, the temperature control program sets, as the control method of the main unit and the auxiliary unit, a third heating control method of adjusting only the heating output of the main unit while stopping the heating output of the auxiliary unit.

13. The liquid chromatograph according to claim 9, wherein temperature range holding section divides and holds the set temperature-neighborhood range as a first set temperature-neighborhood range that is a temperature range that is lower than the set temperature and a second set temperature-neighborhood range that is a temperature range that is higher than the set temperature, and wherein the temperature control program sets, as the control method of the main unit and the auxiliary unit, a first fine control method of adjusting the cooling output of the main unit while maintaining constant the heating output of the auxiliary unit when the temperature range to which the outside temperature belongs is the first set temperature-neighborhood range, and a second fine control method of adjusting the heating output of the auxiliary unit while maintaining constant the cooling output of the main unit when the temperature range to which the outside temperature belongs is the second set temperature-neighborhood range.

14. The liquid chromatograph according to claim 8, further comprising:

a temperature range setting portion for setting the temperature ranges based on the set temperature, and causing the temperature range holding section to hold the temperature ranges.

* * * * *